(12) United States Patent
Yu et al.

(10) Patent No.: US 10,195,442 B2
(45) Date of Patent: Feb. 5, 2019

(54) METHODS AND SYSTEMS FOR MULTI-SITE PACING

(71) Applicant: Cardiac Pacemakers, Inc., St. Paul, MN (US)

(72) Inventors: Yinghong Yu, Shoreview, MN (US); Qi An, Blaine, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/074,639

(22) Filed: Mar. 18, 2016

(65) Prior Publication Data

US 2016/0271393 A1   Sep. 22, 2016

Related U.S. Application Data

(60) Provisional application No. 62/135,357, filed on Mar. 19, 2015.

(51) Int. Cl.
*A61N 1/36* (2006.01)
*A61N 1/368* (2006.01)
(Continued)

(52) U.S. Cl.
CPC .......... *A61N 1/3684* (2013.01); *A61B 5/0402* (2013.01); *A61N 1/056* (2013.01); *A61N 1/3627* (2013.01)

(58) Field of Classification Search
CPC .... A61N 1/3627; A61N 1/368; A61N 1/3684; A61N 1/3686
See application file for complete search history.

(56) References Cited

U.S. PATENT DOCUMENTS 8,694,094 B1   4/2014   Ryu et al.
8,768,465 B2   7/2014   Ghosh et al.
(Continued)

OTHER PUBLICATIONS

Ploux, Sylvain, et al., "Acute electrical and hemodynamic effects of multisite left ventricular pacing for cardiac resynchronization therapy in the dyssynchronous canine heart", Heart Rhythm, v.11, iss.1, Jan. 2014, (118-125).

*Primary Examiner* — Allen Porter, Jr.
(74) *Attorney, Agent, or Firm* — Schwegman Lundberg & Woessner, P.A.

(57) ABSTRACT

Systems and methods for determining multiple sites for multi-site cardiac stimulation are disclosed. The system can comprise an electrostimulation circuit that can deliver electrostimulation to one or more candidate sites in at least one chamber of the heart, such as a left ventricle of the heart, within the same cardiac cycle. The system can sense a physiologic signal during the electrostimulation of the heart, determine activation timings from first and second sets of physiologic signals respectively sensed at the plurality of candidate sites when the heart undergoes specified intrinsic activities or stimulation, and determine at least first and second selected sites, among a plurality of candidate sites, using the respective activation timings. The system can deliver multi-site stimulation such as to the first and second selected sites during a same cardiac cycle, simultaneously or separated by a specified temporal offset.

19 Claims, 5 Drawing Sheets

(51) Int. Cl.
*A61N 1/362* (2006.01)
*A61B 5/0402* (2006.01)
*A61N 1/05* (2006.01)

(56) References Cited

U.S. PATENT DOCUMENTS

| | | | |
|---|---|---|---|
| 2010/0268059 A1* | 10/2010 | Ryu | A61B 5/042 600/407 |
| 2011/0004264 A1* | 1/2011 | Siejko | A61N 1/371 607/28 |
| 2013/0261473 A1* | 10/2013 | Xi | A61B 5/0215 600/486 |
| 2013/0261687 A1* | 10/2013 | Xi | A61N 1/3686 607/18 |
| 2014/0005740 A1 | 1/2014 | Chosh et al. | |

* cited by examiner

METHODS AND SYSTEMS FOR MULTI-SITE PACING

CLAIM OF PRIORITY

This application claims the benefit of priority under 35 U.S.C. § 119(e) of U.S. Provisional Patent Application Ser. No. 62/135,357, filed on Mar. 19, 2015, which is herein incorporated by reference in its entirety.

TECHNICAL FIELD

This document relates generally to medical devices, and more particularly, to devices and methods for stimulating excitable tissue and evaluating resultant physiologic response.

BACKGROUND

Congestive heart failure (CHF) is a leading cause of death in the United States. CHF occurs when the heart is unable to adequately supply enough blood to maintain a healthy physiological state. CHF can be treated by drug therapy, or by an implantable medical device (IMD) such as for providing cardiac pacing therapies, including resynchronization therapy (CRT) to correct cardiac dyssynchrony within a ventricle or between ventricles.

The IMD can chronically stimulate excitable tissues or organs, such as a heart, to treat abnormal cardiac rhythms or to help improve cardiac performance in a patient with CHF. Such ambulatory medical devices can have at least first and second electrodes that can be positioned within the heart or on a surface of the heart for contacting the cardiac tissue. The electrodes can be electrically coupled to an electronics unit such as a pulse generator, such as via a lead, and can be used to deliver one or more electrostimulations to the heart, such as to restore or to improve the normal heart function.

OVERVIEW

Cardiac stimulation using an implantable medical device (IMD) can involve one or more implantable leads that can be transvascularly inserted into one of the heart chambers, such as an atrium or a ventricle. Stimulation of the heart can be accomplished through direct myocardium stimulation using at least first and second electrodes that can be electrically connected to the IMD and in close contact with the cardiac tissue. The electrodes can be positioned along the one or more implantable leads. The stimulation can be provided at specified stimulation strength (e.g., stimulation energy) sufficient to capture the heart tissue, that is, the stimulation can effectively cause depolarization propagating to a part or the entirety of the heart.

During the CRT therapy, synchronized stimulation can be applied to the left ventricle (LV) and the right ventricle (RV) of a heart. Conventionally, there can be one RV pacing site and one LV pacing site. Stimulation of multiple sites on a chamber of the heart, such as pacing at multiple LV sites (which is known as multi-site LV pacing), has been proposed as an alternative to the conventional single site CHF therapy. Compared to the CRT therapy with single site LV pacing, multi-site LV pacing can be more beneficial to some patients at least due to its more effective recruitment of excitable cardiac tissues. Such benefits can include improved cardiac hemodynamic outcome in some CHF patients. The multi-site pacing can involve electrostimulation delivered at two or more sites in at least one heart chamber (such as LV) within a cardiac cycle, such as simultaneous stimulation or separated by a specified temporal offset less than a sensed or paced time interval value of the cardiac cycle.

Although multi-site pacing may be more beneficial than the conventional CRT therapy, multi-site pacing may require more energy than single site pacing, and may also increase the complexity of system design and operation. Additionally, identifying patients that are more likely to benefit from multi-site pacing and selecting the pacing sites among the available candidate sites can be both more clinically challenging and more technically complex when compared to selecting a single pacing site as in the conventional CRT therapy. For example, the effective pacing sites can be affected by a variety of factors including anatomy and pathophysiology of a patient's heart (such as myocardial infarction), lead or electrode positioning on or within the heart, and configurations of the pacing vector and the stimulation parameters, among others. The present inventors have recognized, among other things, that there remains a demand for improved systems and methods for identifying proper pacing sites for multi-site cardiac stimulation, so as to improve the therapy outcome.

This document discusses, among other things, a system for determining multiple sites for multi-site cardiac stimulation. The system can comprise an electrostimulation circuit that can deliver electrostimulation to one or more candidate sites in at least one chamber of the heart, such as multi-site electrostimulation within the same cardiac cycle. The system can sense a physiologic signal during the electrostimulation of the heart. The system can include a stimulation site selector circuit which can determine activation timings from first and second sets of physiologic signals respectively sensed at the plurality of candidate sites when the heart undergoes specified intrinsic activities or stimulation. The stimulation site selector circuit can determine at least first and second selected sites, among a plurality of candidate sites, using the respective activation timings. The electrostimulation circuit can deliver electrostimulation to the first and the at least the second selected sites during a same cardiac cycle, simultaneously or separated by a specified temporal offset less than a sensed or paced interval value of a cardiac cycle.

Example 1 can include a system that comprises an electrostimulation circuit configured to deliver electrostimulation to one or more candidate sites in at least one chamber of a heart, a physiologic sensor circuit configured to sense a physiologic signal including during the electrostimulation of the one or more candidate sites, and a stimulation site selector circuit that is in communication with the physiologic sensor circuit. The stimulation site selector circuit can determine the first activation timing using first physiologic signals sensed by the physiologic sensor circuit at the one or more candidate sites, and determine the second activation timing using second physiologic signals sensed by the physiologic sensor circuit at the one or more candidate sites during an electrostimulation of at least the first selected site. The stimulation site selector circuit can determine the first selected site in response to a first activation timing, associated with the first selected site, meeting a first activation timing criterion, and determine the second selected site in response to a second activation timing, associated with the at least the second selected site, meeting a second activation timing criterion. The system can include an output circuit that can generate human-perceptible presentation of information including the selected stimulation sites.

Example 2 can include, or can optionally be combined with the subject matter of Example 1, to optionally include one or more electrodes electrically coupled to the electrostimulation circuit. The one or more electrodes can be removably and respectively positioned at one or more left ventricular (LV) sites in a left ventricle (LV) of the heart. The electrostimulation circuit can be configured to deliver electrostimulation to the one or more LV sites using the respective one or more electrodes. The physiologic sensor circuit can be configured to sense respective physiologic signal from the one or more LV sites using the respective one or more electrodes.

Example 3 can include, or can optionally be combined with the subject matter of Example 2, to optionally include one or more electrodes in LV which can be distributed on at least one lead configured to be placed in the LV and electrically coupled to the electrostimulation circuit.

Example 4 can include, or can optionally be combined with the subject matter of one or any combination of Examples 2 through 3 to include, the physiologic sensor circuit that can be configured to sense respective cardiac electrical signals at the one or more LV sites during an intrinsic heart rhythm, and to detect respective depolarization at the one or more LV sites using the sensed cardiac electrical signals. The stimulation site selector circuit can be configured to determine first respective activation timings, for the one or more LV sites, using the detect respective depolarization at the one or more LV sites, and determine the first selected LV site corresponds to the latest activation timing among the one or more LV sites.

Example 5 can include, or can optionally be combined with the subject matter of Example 4, to optionally include the stimulation site selector circuit that can be configured to determine the first respective activation timings including time intervals between a reference time and the detected depolarization at the one or more LV sites.

Example 6 can include, or can optionally be combined with the subject matter of Example 5, to optionally include the reference time that can include timing of a Q wave or timing of a sensed or paced activation at a right ventricle (RV).

Example 7 can include, or can optionally be combined with the subject matter of one or any combination of Examples 2 through 6 to include, the physiologic sensor circuit that can be configured to sense respective cardiac electrical signals at the one or more LV sites during an electrostimulation of a site in a right atrium (RA), and to detect respective depolarization at the one or more LV sites using the sensed cardiac electrical signals. The stimulation site selector circuit can be configured to determine first respective activation timings including time intervals between the electrostimulation of the RA and the detected depolarization at the one or more LV sites, and to determine the first selected LV site that corresponds to the latest activation timing among the one or more LV sites.

Example 8 can include, or can optionally be combined with the subject matter of one or any combination of Examples 2 through 7 to include, the physiologic sensor circuit that can further be configured to sense respective cardiac electrical signals at the one or more LV sites, other than the first selected LV site, during the electrostimulation of the first selected LV site, and to detect respective depolarization at the one or more LV sites using the sensed cardiac electrical signals. The stimulation site selector circuit can further be configured to determine second respective activation timings including time intervals between the electrostimulation at the first selected LV site and the detected depolarization at the one or more LV sites, and to determine a second selected LV site that corresponds to the latest activation timing among the one or more LV sites other than the first selected LV site, when the latest activation timing exceeds a specified threshold.

Example 9 can include, or can optionally be combined with the subject matter of one or any combination of Examples 2 through 8 to include, the physiologic sensor circuit than can further be configured to sense respective cardiac electrical signals at the one or more LV sites, other than the first and second selected LV sites, during the electrostimulation of one or both of the first and second selected LV sites, and to detect respective depolarization at the one or more LV sites using the sensed cardiac electrical signals. The stimulation site selector circuit can further be configured to determine third respective activation timings including time intervals between the electrostimulation at one or both of the first and second selected LV sites and the detected depolarization at the one or more LV sites, and to determine a third selected LV site that corresponds to the latest activation timing among the one or more LV sites other than the first and second selected LV sites, when the latest activation timing exceeds a specified threshold.

Example 10 can include, or can optionally be combined with the subject matter of Example 9, to optionally include the stimulation site selector circuit that can be configured to determine the third respective activation timings during simultaneous electrostimulation of both the first and second selected LV sites.

Example 11 can include, or can optionally be combined with the subject matter of Example 9, to optionally include the stimulation site selector circuit that can be configured to determine the third respective activation timings during asynchronous electrostimulation of the first and second selected LV sites separated by a specified latency.

Example 12 can include, or can optionally be combined with the subject matter of one or any combination of Examples 1 through 11 to include, the physiologic sensor circuit than can be configured to sense the physiologic signal including a signal indicative of cardiac mechanical activity.

Example 13 can include, or can optionally be combined with the subject matter of one or any combination of Examples 1 through 12 to include, the physiologic sensor circuit that can be further configured detect a first hemodynamic response to an electrostimulation of the first selected site, or a second hemodynamic response to an electrostimulation of the at least the second selected site; and the stimulation site selector circuit that can be further configured to reconfirm the first selected site in response to the first hemodynamic response meeting a first specified criterion, or to reconfirm the at least the second selected site in response to the second hemodynamic response meeting a second specified criterion.

Example 14 can include, or can optionally be combined with the subject matter of one or any combination of Examples 1 through 13 to include, a therapy controller circuit coupled to the electrostimulation circuit and the stimulation site selector circuit. The therapy controller circuit can be configured to program the electrostimulation circuit to deliver electrostimulation to the first and the at least the second selected sites during a same cardiac cycle.

Example 15 can include, or can optionally be combined with the subject matter of Example 1, to optionally include a stimulation vector selector circuit that can be configured to select one or more stimulation vectors from a plurality of candidate stimulation vectors. The selected one or more stimulation vectors can respectively include an electrode positioned at the first selected site or the at least the second selected site. The electrostimulation circuit can deliver electrostimulation according to the select one or more stimulation vectors.

Example 16 can include a method for stimulating a heart using an electrostimulation device. The method can comprise the operations of receiving physiologic signals at one or more candidate sites in at least one chamber of the heart obtained during an intrinsic heart rhythm, and detecting respective depolarization at the one or more candidate sites using the received physiologic signals, determining first respective activation timings for the one or more candidate sites using the respective physiologic signals obtained during the intrinsic heart rhythm, determining a first selected site in response to the first respective activation timings meeting a first activation timing criterion, receiving physiologic signals at the one or more candidate sites in the at least one chamber of the heart, other than the first selected site, obtained during electrostimulation of the first selected site, determining second respective activation timings for the one or more candidate sites other than the first selected site using the respective physiologic signals obtained during electrostimulation of the first selected site, determining at least a second selected site in response to the second respective activation timing meeting a second activation timing specified criterion, and delivering electrostimulation to the first and the at least the second selected sites. The method includes generating human-perceptible presentation of information including the selected stimulation sites.

Example 17 can include, or can optionally be combined with the subject matter of Example 16, to optionally include an operation of delivering electrostimulation can include delivering electrostimulation to the first and the at least the second selected sites in the LV during the same cardiac cycle, simultaneously or separated by a specified temporal offset less than a sensed or paced interval value of the third cardiac cycle.

Example 18 can include, or can optionally be combined with the subject matter of Example 16, to optionally include an operation of detecting respective depolarization at the one or more candidate sites using the received physiologic signals obtained during the intrinsic rhythm. The first respective activation timings can include time intervals between a reference time and the detected depolarization at the one or more LV sites, and the reference time can include timing of a Q wave or timing of a sensed or paced activation at a right ventricle (RV).

Example 19 can include, or can optionally be combined with the subject matter of Example 16, to optionally include an operation of determining the first selected site that can include determining the first selected site that corresponds to the latest activation timing among the one or more candidate sites.

Example 20 can include, or can optionally be combined with the subject matter of Example 16, to optionally include an operation of detecting respective depolarization at the one or more candidate sites using the received physiologic signals obtained during the electrostimulation of the first selected site. The second respective activation timings can include time intervals between the electrostimulation at the first selected site and the detected depolarization at the one or more candidate sites.

Example 21 can include, or can optionally be combined with the subject matter of Example 16, to optionally include the operation of determining the second selected site that can include determining the at least the second selected site that corresponds to the latest activation timing among the one or more candidate sites, other than the first selected site, when the latest activation timing exceeds a specified threshold.

Example 22 can include, or can optionally be combined with the subject matter of Example 16, to optionally include the operations of receiving physiologic signals at the one or more candidate sites, other than the first and second selected sites, obtained during electrostimulation of one or both of the first and second selected sites, detecting respective depolarization at the one or more candidate sites using the sensed cardiac electrical signals, determining third respective activation timings including time intervals between the electrostimulation at one or both of the first and second selected sites and the detected depolarization at the one or more candidate sites, and determining a third selected site that corresponds to the latest activation timing among the one or more candidate sites other than the first and second selected sites, when the latest activation timing exceeds a specified threshold.

Example 23 can include, or can optionally be combined with the subject matter of Example 16, to optionally include the operations of detecting a first hemodynamic response to an electrostimulation of the first selected site, or a second hemodynamic response to an electrostimulation of the second selected site, and reconfirming the first selected site in response to the first hemodynamic response meeting a first specified criterion, or reconfirming the second selected site in response to the second hemodynamic response meeting a second specified criterion.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for determining sites in at least one chamber of a heart for multi-site stimulation. The stimulation, such as an electrostimulation sequence, can be applied to multiple sites of the heart such as multi-sites of the left ventricle (LV) of the heart, to restore or improve cardiac performance. The physiologic signals sensed at multiple sites during cardiac electrostimulation at a specified site or when the heart undergoes a specified condition, such as during an intrinsic heart rhythm, can be analyzed to determine two or more stimulation sites at the heart. The selected stimulation sites can be stimulated simultaneously or asynchronously within a cardiac cycle to achieve desired cardiac hemodynamics.

Figure 1:
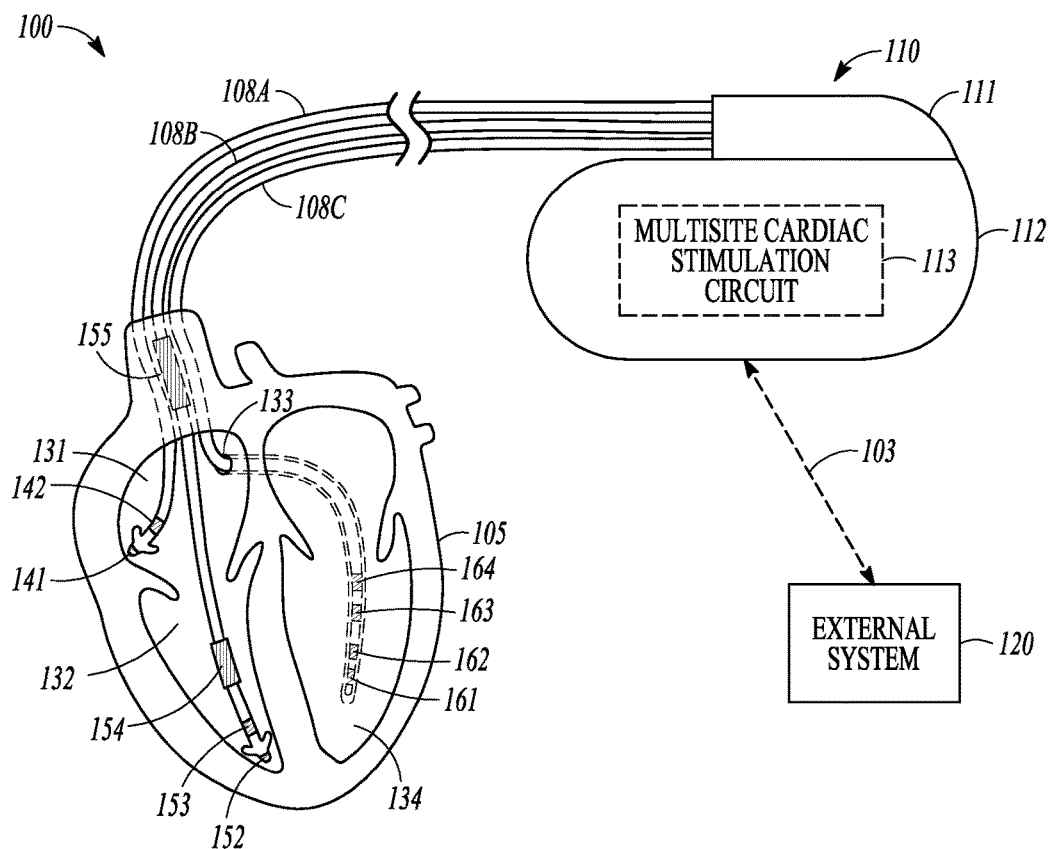
FIG. 1 illustrates an example of a Cardiac Rhythm Management (CRM) system and portions of an environment in which the CRM system can operate.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing the LV electrogram and optionally allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a multisite cardiac stimulation circuit 113. The multisite cardiac stimulation circuit 113 can be configured to detect physiologic responses to electrostimulation at one or more candidate sites of the heart 105, such as electrostimulation of the left ventricle (LV) 134 via one or more of the electrodes 161-164 on the lead 108C. The physiologic response can include cardiac electrical signals or cardiac mechanical signals. The multisite cardiac stimulation circuit 113 can determine first activation timing using the sensed physiologic signal, and determine a first selected site among the one or more candidate sites in response to the first activation timing meeting a specified first activation timing criterion. The multisite cardiac stimulation circuit 113 can additionally determine second activation timing using second physiologic signals sensed at the one or more candidate sites during an electrostimulation of at least the first selected site, and determine at least the second selected site in response to the second activation timing meeting a second activation timing criterion. The multisite cardiac stimulation circuit 113 can be programmed to deliver multi-site electrostimulation to the selected sites including the first and at least the second selected sites. Examples of the multisite cardiac stimulation circuit 113 are described below, such as with reference to FIGS. 2-4.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The multisite cardiac stimulation circuit 113 can be implemented at the external system 120 such as using data extracted from the IMD 110 or data stored in a memory within the external system 120. Portions of the multisite cardiac stimulation circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices. The CRM system 100 may alternatively or additionally include one or more untethered ambulatory medical devices such as an implantable electrostimulators configured to be deployed at various target sites such as endocardial or epicardial sites. The untethered devices need not be tethered to another device by a leadwire or other wired connection. One or more electrodes may be associated with an outer surface of an untethered device to sense a physiological signal or to deliver electrostimulation to the target site. In some examples, the IMD 110 or a subcutaneous or wearable device may be configured to communicate with the one or more untethered devices such as via a wireless communication link, and provide instructions to the one or more untethered devices on when to deliver the electrostimulation at the various target sites.

Figure 2:
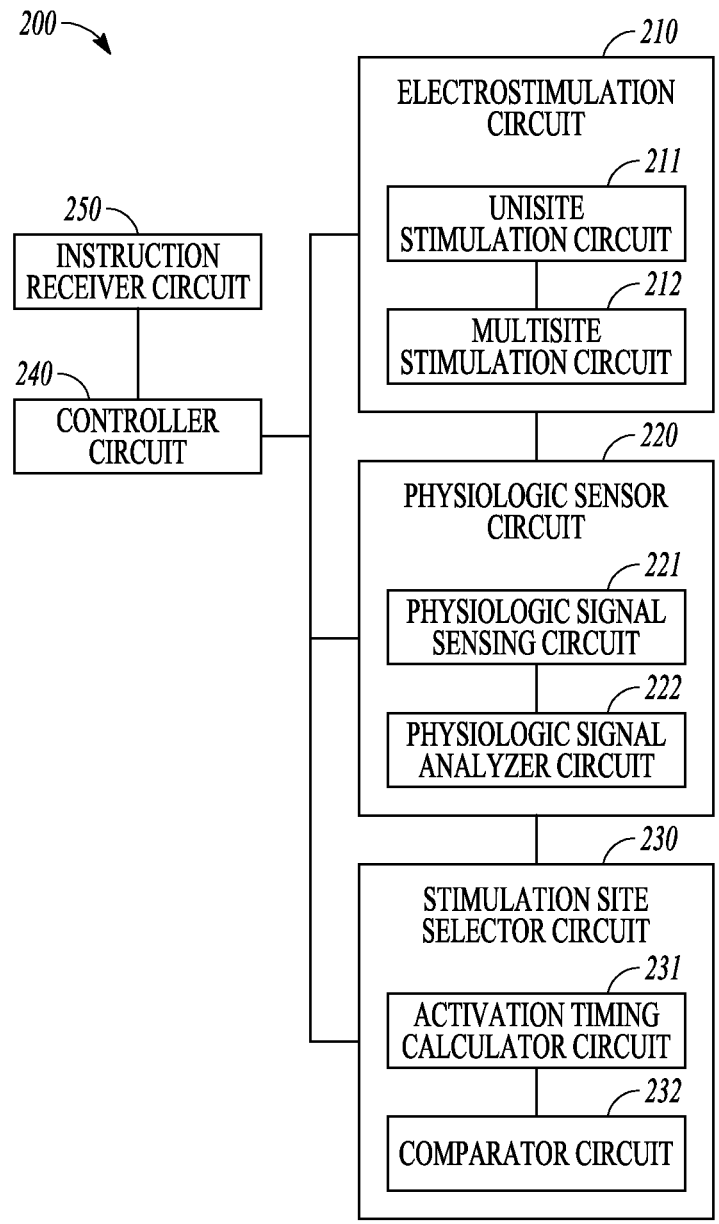
FIG. 2 illustrates an example of a multisite electrostimulation circuit.

FIG. 2 illustrates an example of a multisite electrostimulation circuit 200, which can be an embodiment of the multisite cardiac stimulation circuit 113. The multisite electrostimulation circuit 200 can include one or more of an electrostimulation circuit 210, a physiologic sensor circuit 220, a stimulation site selector circuit 230, a controller circuit 240, and an instruction receiver circuit 250.

The electrostimulation circuit 210 can be configured to deliver electrostimulation to one or more candidate sites of a heart, such as one or more candidate sites of at least one chamber of the heart. The electrostimulation, such as a pulse train, can be produced by the IMD 100 or an external pulse generator, and delivered to the one or more candidate sites of the heart via a pacing delivery system such as one or more of the leads 108A-C and the respectively attached electrodes. The electrostimulation can be delivered between an anode and a cathode. The anode and the cathode form a pacing vector. The electrostimulation can include a unipolar or a bipolar pacing configuration. The unipolar pacing can involve stimulation between an electrode positioned at or near a target stimulation site of the heart (such as an electrode on one of the leads 108A-C), and a return electrode such as the IMD can 112. The bipolar pacing can involve stimulation between two electrodes on one or more of the leads 108A-C.

As illustrated, the electrostimulation circuit 210 can include a uni-site stimulation circuit 211 and a multi-site stimulation circuit 212. The uni-site stimulation circuit 211 can be configured to deliver uni-site electrostimulation that involves stimulating one specified site of the heart. The multi-site stimulation circuit 212 can be configured to deliver electrostimulation to two or more sites of the heart within the same cardiac cycle. In an example, the multi-site stimulation circuit 212 can deliver an electrostimulation to two or more sites with a cardiac cycle simultaneously, or separated by a specified temporal offset less than a sensed or paced time interval value of the cardiac cycle. As an example, the temporal offset can be between 0-100 msec.

The two or more sites for electrostimulation can include anatomical regions inside, or on an epicardial surface of, one or more heart chambers, including right atrium (RA), right ventricle (RV), left atrium (LA), and left ventricle (LV), or tissues surrounding any of the chambers. In an example, the multi-site stimulation circuit 212 can deliver electrostimulation to at least a site at RV and a site at LV. In another example, the multi-site stimulation circuit 212 can deliver electrostimulation to two or more sites at the same chamber, such as two or more sites in LV which is hereinafter referred to as "multi-site LV pacing." The multi-site LV pacing can be achieved using two or more LV pacing vectors. For each LV pacing vector, at least one of the anode or the cathode can be selected from the two or more electrodes on the LV lead 133 (such as electrodes 161-164). In an example, the electrostimulation circuit 210 can deliver multi-site LV pacing using one or more of a bipolar pacing between two LV electrodes, a bipolar pacing between an LV electrode and a RV or RA electrode, a tripolar pacing between one or more LV electrodes and a RV or RA electrode, or a unipolar pacing between an LV electrode and the IMD can 112. In some examples, one or more LV electrodes can be distributed in one or more LV leads, catheters, or non-tethered pacing units. The electrostimulation can be delivered to the two or more sites within a cardiac cycle, such as simultaneous stimulation or asynchronous stimulation separated by a specified temporal offset less than a sensed or paced time interval value of the cardiac cycle.

The physiologic sensor circuit 220 can include a physiologic signal sensing circuit 221 and a physiologic signal analyzer circuit 222. The physiologic signal sensing circuit 221 can sense a physiologic signal under a specified condition, such as when the heart undergoes an intrinsic rhythm such as a sinus rhythm, or when the heart is stimulated in accordance with a specified stimulation protocol. The physiologic signal can include cardiac electrical signals such as electrocardiograms (ECGs) such as sensed by using electrodes non-invasively attached to the body surface, subcutaneous ECGs such as sensed by using subcutaneously placed electrodes, or intracardiac electrograms (EGMs) such as sensed by using electrodes on one or more of the leads 108A-C or the can 112. Additionally or alternatively, the physiologic signals can also include signals indicative of cardiac mechanical activities such as contractions of an atrium or a ventricle as a response to an intrinsic heart rhythm or a stimulation of the heart. In an example, the cardiac mechanical activities can include a signal sensed from an ambulatory accelerometer or a microphone configured to sense the heart sounds in a patient. In an example, the cardiac mechanical activities can include a signal sensed from an impedance sensor configured to sense cardiac or thoracic impedance change as a result of cyclic cardiac contractions. The cardiac mechanical signals can include pressure sensor signals or any other sensor signals indicative of cardiac contractions.

The physiologic signal analyzer circuit 222 can process the sensed physiologic signal (such as that produced by the physiologic signal sensing circuit 221), including amplification, digitization, filtering, or other signal conditioning operations. In an example, the physiologic signal analyzer circuit 222 can detect one or more characteristic signal features from the cardiac electrical signal or cardiac mechanical signal. The characteristic signal features can include temporal or morphological features indicative of intrinsic cardiac activity such as a P wave, Q wave, R wave, QRS complex, or T wave that can be detected from a surface ECG, a subcutaneous ECG, or an intracardiac EGM. The characteristic signal features can also be indicative of evoked cardiac activity such as evoked electrical or mechanical activation in response to an electrostimulation of the heart. The physiologic signal analyzer circuit 222 can detect the characteristic signal features by comparing an intensity measure of the physiologic signal to a specified threshold. A signal feature is deemed detected if the intensity measure exceeds the specified threshold or beyond a specified margin. Examples of the intensity measure can include signal amplitude, slope or rate of change of signal amplitude, amplitude of a transformed physiologic signal such as integrated signal, or a frequency-domain measurement such as power spectral density.

The physiologic sensor circuit 220 can sense and analyze two or more physiologic signals simultaneously or sequentially. The two or more physiologic signals can be sensed from respective two or more sites on or within a chamber, such as a left ventricle (LV), of the heart. In an example, the physiologic sensor circuit 220 can sense two or more physiologic signals via respective sensing vectors that include respective electrodes removably positioned at a chamber of the heart. For example, the physiologic sensor circuit 220 can sense two or more physiologic signals from two or more LV sites using respective sensing vectors each including at least one of electrodes 161-164 on the LV lead 133. An example of the LV sensing vector can include a bipolar sensing vector such as between a pair of electrodes selected among 161-164, or between one of the electrodes 161-164 and another electrode positioned on a different chamber or attached to a different lead (such as one of electrodes 152-155 on the RV lead 108B, or electrodes 141 or 142 on the RA lead 108A). Another example of the LV sensing vector can include a unipolar sensing vector such as between one of the electrodes 161-164 and the can 112.

The stimulation site selector circuit 230 can be in communication with the physiologic sensor circuit 220, and configured to determine one or more stimulation sites in a chamber such as left ventricle (LV) of the heart for electrostimulation such as by using the sensed physiologic signal produced by the physiologic sensor circuit 220. The stimulation site selector circuit 230 can be implemented as a part of a microprocessor circuit within the multisite electrostimulation circuit 200. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the functions, methods, or techniques described herein. The stimulation site selector circuit 230 can include an activation timing calculator circuit 231 and a comparator circuit 232.

The activation timing calculator circuit 231 can compute respective activation timings of the characteristic signal features from the two or more sensed physiologic signals such as produced by the physiologic sensor circuit 220. The activation timings can be computed as a time interval between the detected characteristic signal features (such as intrinsic or evoked cardiac events) and a reference time. The reference time can include timing of a Q wave, timing of a sensed or paced activation at a location in the heart such as right ventricle (RV), or timing of the stimulation the evokes the physiologic responses as sensed by the physiologic sensor circuit 220. In an example, the activation timing calculator circuit 231 can compute a first set of activation timings using first physiologic signals sensed from multiple sites on a chamber such as a LV of the heart. The first physiologic signals can be sensed when the heart undergoes a specified intrinsic rhythm such as sinus rhythm or when the heart is stimulated according to a specified stimulation protocol such as RA pacing. Each of the first activation timings can be computed as a time interval between the detected characteristic signal feature and a Q wave or timing of a stimulation artifact of the RA pacing. In an example, the activation timing calculator circuit 231 can additionally compute at least a second set of activation timings using second physiologic signals sensed from multiple sites on the chamber such as the LV of the heart. The second physiologic signals can be sensed when the heart is stimulated according to a specified stimulation protocol such as electrostimulation of at least a first selected site which is determined based on a comparison of the first set of activation timings. Each of the second activation timings can be computed as a time interval between the detected characteristic signal feature and the electrostimulation at the first selected site.

The comparator circuit 232 can be configured to compare the activation timings associated with the two or more sensed physiologic signals, and determine a selected site among the one or more candidate sites of the heart chamber when the comparison meets a specified activation timing criterion. A selected site can be determined as the one that corresponds to the latest activation timing among the one or more candidate sites of the heart chamber. A selected site can be determined further in response to the latest activation timing exceeding a predetermined threshold or falling within a specified range. In an example, the comparator circuit 232 can determine a first selected site that corresponds to the latest activation timing among the first set of activation timings. The physiologic sensor circuit 220 can sense the second physiologic signals during the electrostimulation of the first selected site. The activation timing calculator circuit 231 can compute at least the second set of activation timings using the second physiologic signals, and the comparator circuit 232 can determine a second selected site that corresponds to the latest activation timing among the second set of activation timings. Examples of the stimulation site selector for multiple stimulation site selection are discussed below, such as with reference to FIG. 3.

In an example, the information of the selected stimulation sites, along with other device information, can be displayed or otherwise presented in a human-perceptible medium format to a system user. In an example, the electrostimulation circuit 210 can program multi-site stimulation based at least on the selected stimulation sites, such as by adjusting one or more stimulation intensity parameters (e.g., amplitude, pulse width, duty cycle, duration, or frequency), stimulation modes or configuration of stimulation vectors for the selected stimulation sites. The electrostimulation circuit 210 can deliver electrostimulation to the first and the at least the second selected sites during the same cardiac cycle, simultaneously or separated by a specified temporal offset less than a sensed or paced interval value of a cardiac cycle.

The controller circuit 240 can receive external programming input from the instruction receiver circuit 250 to control the operations of the electrostimulation circuit 210, the physiologic sensor circuit 220, the stimulation site selector circuit 230, and the data flow and instructions between these components and respective subcomponents. Examples of the instructions received by instruction receiver 240 can include parameters for delivering electrostimulation including stimulation vector configurations and stimulation frequency and energy, sensing vector configurations, sensing and processing physiologic signals, calculating activation timings, and determining selected stimulation sites based on the comparison of the activation timings. The instruction receiver circuit 250 can include a user interface configured to present programming options to a system user, and receive the system user's programming input. In an example, at least a portion of the instruction receiver circuit 250, such as the user interface, can be implemented in the external system 120.

In an example, the multisite electrostimulation circuit 200 can include a stimulation vector selector circuit in addition to, or in lieu of, the stimulation site selector circuit 230. The stimulation vector selector circuit can be configured to select one or more stimulation vectors from a plurality of candidate stimulation vectors. Each stimulation vector can include an anode and a cathode electrode. In an example, the cathode or the anode can include an electrode positioned at a selected site at a heart chamber (such as the LV). In an example, the stimulation vector selector circuit can select the one or more selected stimulation vectors that respectively include a cathode positioned at the selected stimulation sites corresponding to latest activation timing, such as determined by the stimulation site selector circuit 230. In an example, the stimulation vector selector circuit can use the activation timing and one or more additional parameters to determine the one or more selected stimulation vectors. Examples of the additional parameters can include lead impedance as sensed between the stimulation electrodes, pacing threshold indicative of minimal energy required to capture the cardiac tissue, absence of or significance of phrenic nerve stimulation during stimulation, power consumption by stimulation and impact on longevity of the pulse generator, etc. The electrostimulation circuit 210 can deliver multisite electrostimulation according to the selected one or more stimulation vectors.

Figure 3:
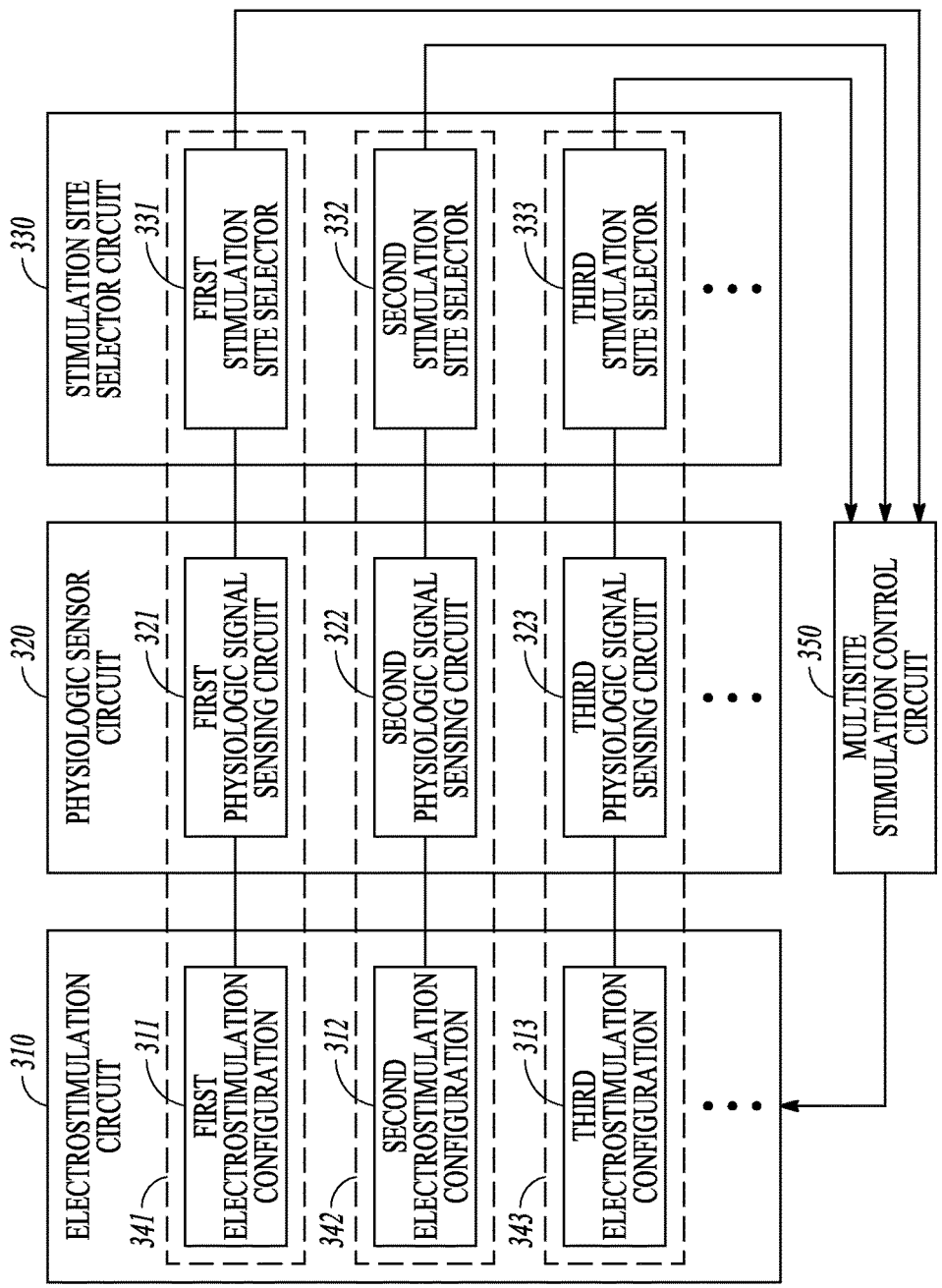
FIG. 3 illustrates an example of a multiple stimulation site selection circuit for use in multi-site LV pacing.

FIG. 3 illustrates an example of a multiple stimulation site selection circuit 300 for use in multi-site LV pacing, which can be an embodiment of at least part of the multisite electrostimulation circuit 200. The multiple stimulation site selection circuit 300 can include an electrostimulation circuit 310 which can be an embodiment of the electrostimulation circuit 210, a physiologic sensor circuit 320 which can be an embodiment of the physiologic sensor circuit 220, and a stimulation site selector circuit 330 which can be an embodiment of the stimulation site selector circuit 230.

The electrostimulation circuit 310 can include multiple configurations for generating and delivering electrostimulation to at least one chamber of the heart, such as a first electrostimulation configuration 311, a second electrostimulation configuration 312, and a third electrostimulation configuration 313, among other stimulation configurations. Various electrostimulation configurations can differ from one another in one or more stimulation parameters, such as stimulation vector configuration. Electrostimulation in accordance with a particular electrostimulation configuration can be used for determining a selected site in the heart chamber.

The physiologic sensor circuit 320 can include multiple subcircuits for sensing multiple physiologic signals from multiple respective sites of the heart chamber, such as multiple sites on the LV, during the delivery of the electrostimulation. As illustrated, the physiologic sensor circuit 320 can include a first physiologic signal sensing circuit 321, a second physiologic signal sensing circuit 322, and a third physiologic signal sensing circuit 323, among other physiologic signal sensing circuits. Various physiologic signal sensing circuits can sense respective set of physiologic signals during electrostimulation according to the respective electrostimulation configuration, and generate characteristic signal features indicative of intrinsic or evoked cardiac activities from the respective physiologic signals.

The electrostimulation circuit 330 can include multiple stimulation site selectors such as a first stimulation site selector 331, a second stimulation site selector 332, and a third stimulation site selector 333, among other stimulation site selectors. Various stimulation site selectors can calculate activation timings of the characteristic signal features associated with respective physiologic signals at multiple sites of the heart chamber, and determine the selected stimulation sites when a comparison of the characteristic signal features meets a specified criterion.

The multiple stimulation site selection circuit 300 can be used for pacing sites selection for multi-site LV pacing as a treatment for heart failure. The multiple selected LV sites, such as N sites $\{P_1, P_2, \ldots, P_N\}$, can be determined sequentially in multiple paths using the subcircuits illustrated in FIG. 3. The N sites at LV can include those where LV electrodes are positioned (such as electrodes 161-164 on the LV lead 108C), or electrodes from other leads or catheters that are placed inside, on the surface of, or otherwise attached to the LV.

A first path 341, comprising the first electrostimulation configuration 311, the first physiologic signal sensing circuit 321, and the first stimulation site selector 331, can be used to determine the first selected LV site among the multiple LV sites. The first electrostimulation configuration 311 can include an RA unipolar or bipolar pacing configuration involving at least one of the RA electrodes 141 or 142. The first physiologic signal sensing circuit 321 can sense the first set of physiologic signals $X=\{X_1(t), X_2(t), \ldots, X_N(t)\}$, where $X_i(t)$ denotes a physiologic signal sensed at LV site $P_i$ during the delivery of the electrostimulation according to the first electrostimulation configuration 311. In an example, no electrostimulation is delivered (that is, the first electrostimulation configuration 311 does not include a particular stimulation configuration), and the first physiologic signal sensing circuit 321 can sense the first set of physiologic signals X representing intrinsic rather than evoked cardiac activities, such as during a sinus rhythm. The first physiologic signal sensing circuit 321 can detect, from each of the physiologic signals $\{X_1(t), X_2(t), \ldots, X_N(t)\}$, a respective characteristic signal feature, such as detected depolarization at the respective LV site. The first stimulation site selector 331 can compute first activation timings $\{Tx\}=\{Tx_1, Tx_2, \ldots, Tx_N\}$, where $Tx_i$ denotes the activation timing of the characteristic signal feature detected from the physiologic signal $X_i(t)$. The activation timing $Tx_i$ can include a time interval between a detected depolarization at the respective LV site $P_i$ and a reference time. In an example when $\{X\}$ are obtained during intrinsic cardiac activity (such as sinus rhythm), the reference time can include timing of a Q wave or timing of a sensed or paced activation at a site in the RV, so that the activation timing $T_i$ can indicate time delay from the Q wave or the RV activation to the detected depolarization at the LV site $P_i$. In another example when $\{X\}$ are obtained during RA pacing, the reference time can include timing of a pacing artifact of the RA pacing, so that the activation timing $T_i$ can indicate time delay from the RA pacing event to the detected depolarization at the LV site $P_i$.

The first stimulation site selector 331 can determine the first selected LV site ($SP_1$), among N sites $\{P_1, P_2, \ldots, P_N\}$, that corresponds to the latest activation timing, such as the longest time delay from the Q wave or the RV activation to the detected depolarization at the LV sites $\{P_1, P_2, \ldots, P_N\}$, or the longest time delay from the RA pacing event to the detected depolarization at the LV sites $\{P_1, P_2, \ldots, P_N\}$. In an example, the first selected LV site ($SP_1$) is selected further in response to the latest activation timing exceeding a specified threshold.

A second path 342, comprising the second electrostimulation configuration 312, the second physiologic signal sensing circuit 322, and the second stimulation site selector 332, can be used to determine the second selected LV site among the multiple LV sites. In an example, a multisite stimulation control circuit 350 can be configured to determine the second electrostimulation configuration 312 using the selected sites such as determined by the various first stimulation site selectors. In an example, the second electrostimulation configuration 312 can include a unipolar or bipolar pacing at the first selected LV site $SP_1$. The second physiologic signal sensing circuit 322 can sense the second set of physiologic signals at all N sites on LV except $SP_1$. For example, if $SP_1$ is determined to be $P_k$, then the second physiologic signal sensing circuit 322 can sense up to N−1 physiologic signals $\{Y\}=\{Y_1(t), Y_2(t), \ldots, Y_{k-1}(t), Y_{k+1}(t), \ldots, Y_N(t)\}$, where $Y_i(t)$ denotes a physiologic signal sensed at LV site $P_i$ during the delivery of the electrostimulation according to the second electrostimulation configuration 312. The second physiologic signal sensing circuit 322 can detect from each of the physiologic signals $\{Y\}$ a respective characteristic signal feature, such as detected depolarization at the respective LV site. The second stimulation site selector 332 can compute second activation timings $\{Ty\}=\{Ty_1, Ty_2, \ldots, Ty_{k-1}, Ty_{k+1}, \ldots, Ty_N\}$, where $Ty_i$ denotes the activation timing of the characteristic signal feature detected from the physiologic signal $Y_i(t)$. The activation timing $Ty_i$ can include a time interval between a detected depolarization at the respective LV site and the electrostimulation at $SP_1$.

The second stimulation site selector 332 can determine the second selected LV site ($SP_2$), among N−1 sites $\{P_1, P_2, \ldots, P_{k-1}, P_{k+1}, \ldots, P_N\}$, that corresponds to the latest activation timing, such as the longest time delay from the electrostimulation at $SP_1$ to the detected depolarization at the LV sites $\{P_1, P_2, \ldots, P_{k-1}, P_{k+1}, \ldots, P_N\}$, provided the latest activation timing exceeding a specified threshold.

A third path 343, comprising the third electrostimulation configuration 313, the third physiologic signal sensing circuit 323, and the third stimulation site selector 333, can be used to determine the third selected LV site among the multiple LV sites. The multisite stimulation control circuit 350 can determine the third electrostimulation configuration 313 to include electrostimulation of one or both of the first ($SP_1$) and second ($SP_2$) selected LV sites. In an example, the third electrostimulation configuration 313 can include simultaneous electrostimulation of both the $SP_1$ and $SP_2$. In another example, the third electrostimulation configuration 313 can include asynchronous electrostimulation of $SP_1$ and $SP_2$ by a specified latency.

The third physiologic signal sensing circuit 323 can sense the third set of physiologic signals at all N sites on LV except $SP_1$ and $SP_2$. The third physiologic signal sensing circuit 323 can sense up to N−2 physiologic signals $\{Z\}$, and detect from each of the physiologic signals $\{Z\}$ a respective characteristic signal feature, such as detected depolarization at the respective LV site. The third stimulation site selector 333 can compute second activation timings $\{Tz\}$ from the respective physiologic signals $\{Z\}$. The activation timing $Tz_i$ can include a time interval between the electrostimulation at $SP_1$ or $SP_2$ and a detected depolarization at the respective LV site. The third stimulation site selector 333 can determine the third selected LV site ($SP_3$), among N−2 sites, that corresponds to the latest activation timing, such as the longest time delay from the electrostimulation at $SP_1$ to the detected depolarization at the LV sites, provided the latest activation timing exceeding a specified threshold.

Although FIG. 3 shows three paths of sequential determination of three LV stimulation sites $SP_1$, $SP_2$ and $SP_3$, the present inventors have contemplated determining additional stimulation sites using similar approach as presented in this document. Generally, when N stimulation sites are provided, up to N sites can be selected using the approach presented in this document. By choosing different threshold values to which the latest activation timing at each path is compared, fewer than N sites can be selected. For example, if at path k the latest activation timing is less than the specified threshold value, the k-th stimulation site selector will not generate a selected site. As such, only k−1 stimulation sites can be selected from N sites, that is, $SP=\{SP_1, SP_2, \ldots, SP_{k-1}\}$.

In some examples, the stimulation site selector circuit 230 or the stimulation site selector circuit 330 can determine a selected stimulation site using a hemodynamic response to the stimulation at the site that corresponds to the latest activation. The hemodynamic response can be used in addition to, or in lieu of, the criterion such as the latest activation timing exceeding a specified threshold. In an example, the hemodynamic response can be used to reconfirm the selected site $SP_k$ determined based on the latest activation timing. For example, when the third stimulation site selector 333 (as illustrated in FIG. 3) determines the third selected site ($SP_3$) that corresponds to the latest activation timing that exceeds a specified threshold, the electrostimulation circuit 310 can generate and deliver a "confirmatory" electrostimulation to the selected site $SP_3$, either alone or in combination with other selected sites (e.g., $SP_1$ or $SP_2$). The physiologic sensor circuit 220 or the physiologic sensor circuit 320 can be configured to sense a hemodynamic signal in response to the confirmatory electrostimulation, and produce one or more hemodynamic parameters using the sensed hemodynamic signal. The stimulation site selector circuit 230 or the stimulation site selector circuit 330 can reconfirm the $SP_3$ as a selected site in response to the one or more hemodynamic parameters meeting a specified criterion such as indicative of an improvement of hemodynamic outcome beyond a specified margin over the stimulation without involving $SP_3$ (e.g., electrostimulation at one or both of $SP_1$ and $SP_2$).

The physiologic sensor circuit 220 or the physiologic sensor circuit 320 can be communicatively coupled to a hemodynamic sensor deployed outside or inside the patient's body, and can sense at least one hemodynamic signal indicative of hemodynamic status of the patient using the hemodynamic sensor. The hemodynamic sensor can include implantable, wearable, or other ambulatory physiologic sensors that directly or indirectly measure dynamics of the blood flow in a heart chamber or in a blood vessel. Examples of the hemodynamic sensors and the physiologic variables to sense can include a pressure sensor configured for sensing arterial pressure, pulmonary artery pressure, left atrial pressure, RV pressure, LV coronary pressure; impedance sensors configured for sensing thoracic impedance or cardiac impedance; a temperature sensor configured for sensing blood temperature; an accelerometer or a microphone configured for sensing one or more heart sounds; an optical sensor such as a pulse oximeter configured for sensing blood oxygen saturation; a chemical sensor configured for sensing central venous pH value.

The physiologic sensor circuit 220 or the physiologic sensor circuit 320 can produce from the sensed hemodynamic signal one or more hemodynamic parameters including, for example, intensity indicators of one or more heart sound components (e.g., S1, S2, S3, or S4 heart sounds) obtained from the sensed heart sound signal; peak, trough, or rate of change of impedance from the cardiac or thoracic impedance signal; peak, trough, or rate of change of blood pressure from the blood pressure signal; peak, trough, or rate of change of a respiration signal; timing information associated with these signal components or characteristics such as a pre-ejection period (PEP), a systolic timing interval (STI), a diastolic timing interval (DTI), or a left ventricular ejection time (LVET). The hemodynamic parameter can also include composite measures using two or more of the STI, the DTI, the PEP, the CL, or the LVET. Examples of the composite measures can include PEP/LVET ratio, STI/DTI ratio, STI/CL ratio, or DTI/CL ratio, among others.

Figure 4:
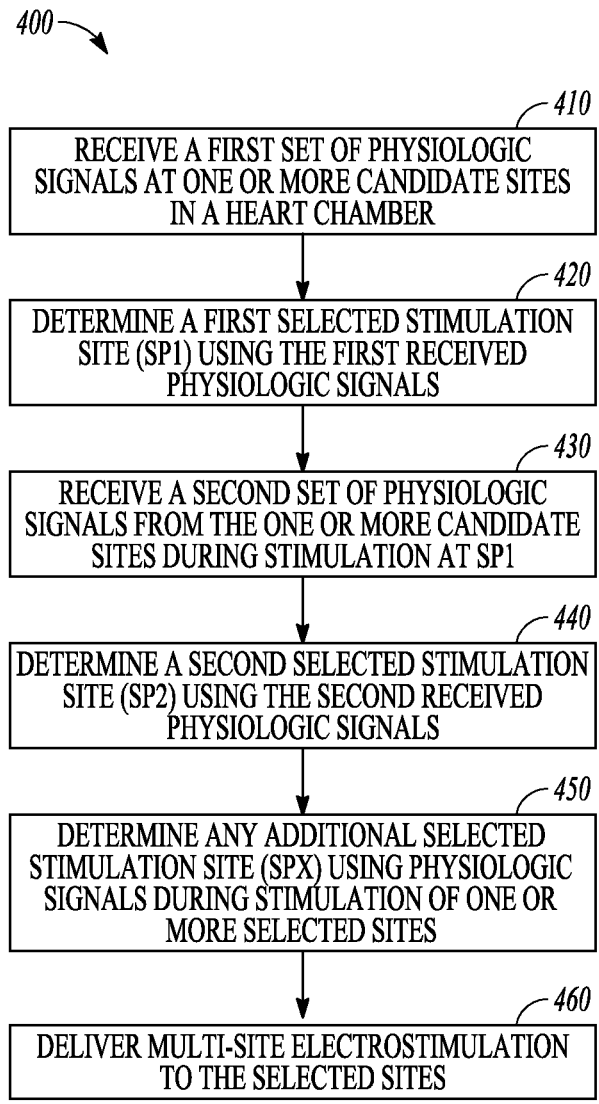
FIG. 4 illustrates an example of a method for multi-site electrostimulation of a heart of a subject.

FIG. 4 illustrates an example of a method 400 for multi-site electrostimulation of a heart of a subject. The method 400 can be implemented and operate in an implantable, wearable, or other ambulatory medical device, or in a remote patient management system. In an example, the method 400 can be performed by the multisite electrostimulation circuit 200 or any modification thereof.

The method 400 can begin at step 410, where a first set of physiologic signals can be received at one or more candidate sites in a chamber of the heart, such as multiple sites on a left ventricle (LV) of the heart where sense or stimulation electrodes (such as electrodes 161-164 on the LV lead 133) are located. The first set of physiologic signals can be sensed under a specified condition, such as when the heart undergoes an intrinsic rhythm such as a sinus rhythm, or when the heart is stimulated in accordance with a specified stimulation protocol, such as during right atrium (RA) pacing. The physiologic signal can include cardiac electrical signals such as electrocardiograms (ECGs) sensed from body surface, subcutaneous ECGs such as sensed by using subcutaneously placed electrodes, or intracardiac electrograms (EGMs) such as sensed by using electrodes on one or more of the leads 108A-C or the can 112. Additionally or alternatively, the physiologic signals can also include signals indicative of cardiac mechanical activities, such as heart sounds signals, blood pressure signals, or other signals indicative of contractions of an atrium or a ventricle as a response to an intrinsic heart rhythm or a stimulation of the heart. At 410 the received first set of the physiologic signals can be processed, and respective characteristic signal features can be detected from the processed first set of physiologic signals. In an example, the characteristic signal features can include depolarization at the one or more candidate sites. In an example, characteristic signal features can include temporal or morphological signal features indicative of intrinsic cardiac activity such as a P wave, Q wave, R wave, QRS complex, or T wave that can be detected from a surface ECG, a subcutaneous ECG, or an intracardiac EGM, or evoked cardiac activity such as evoked electrical or mechanical activation in response to an electrostimulation of the heart.

At 420, a first selected stimulation site ($SP_1$) can be determined using the first set of the received physiologic signals. In an example, activation timings for the one or more candidate sites can be computed using the characteristic signal features, such as the detected depolarization, as obtained from first set of physiologic signals. The activation timings can be computed as a time interval between the detected characteristic signal features (such as intrinsic or evoked cardiac depolarizations) and a reference time (such as a Q wave or timing of a sensed or paced activation at a location in the heart such as a right ventricle). The activation timings can be compared, and the first selected stimulation site $SP_1$ can be determined among the one or more candidate sites when the comparison meets a specified activation timing criterion. For example, the $SP_1$ can be determined as the site corresponds to the latest activation timing among the one or more candidate sites of the heart chamber.

At 430, a second set of physiologic signals can be received at the one or more candidate sites in a chamber of the heart, other than the first selected site $SP_1$. The second set of the physiologic signals can be obtained during electrostimulation of the heart using a stimulation vector involving the first selected site $SP_1$. Such electrostimulation can be in a unipolar or a bipolar stimulation configuration, where an electrode at $SP_1$ can be used as the cathode or anode for stimulation. Similar to the operation at the step 410, the received second set of the physiologic signals can be processed, and respective characteristic signal features can be detected from the processed second set of physiologic signals.

At 440, a second selected stimulation site ($SP_2$) can be determined using the second set of the received physiologic signals. Similar to the operation at the step 420, activation timings for the one or more candidate sites (other than $SP_1$) can be computed using the characteristic signal features, such as the detected depolarization in response to the electrostimulation at $SP_1$. The second selected stimulation site SP2 can be determined among the one or more candidate sites when the comparison meets a specified activation timing criterion. For example, the SP2 can be determined as the site corresponds to the latest activation timing among the one or more candidate sites of the heart chamber when the latest activation timing exceeds a specified threshold.

At 450, additional selected stimulation sites ($SP_x$) other than $SP_1$ and $SP_2$, can be determined using a similar approach as in steps 430-440. For example, if N stimulation sites are provided for sensing and stimulation at a chamber of the heart, up to N sites can be selected using the approach presented in this document. By choosing different threshold values to which the latest activation timing is compared, fewer than N sites can be selected.

In some examples, the method 400 can include additional operation of receiving hemodynamic response to the stimulation at the site that corresponds to the latest activation. The hemodynamic response can be used in addition to, or in lieu of, the criterion such as the latest activation timing exceeding a specified threshold. For example, upon determining the second selected site SP2 at 440, a "confirmatory" electrostimulation can be delivered to the selected site $SP_2$, and a resulting hemodynamic response can be sensed, such as by using a hemodynamic sensor. The hemodynamic response can include arterial pressure, pulmonary artery pressure, left atrial pressure, RV pressure, LV coronary pressure; thoracic impedance or cardiac impedance; blood temperature; one or more heart sounds; blood oxygen saturation; central venous pH value, among others. The selected site $SP_2$ can be reconfirmed when the hemodynamic response meets a specified criterion such as indicative of an improvement of hemodynamic outcome beyond a specified margin over the stimulation without involving $SP_2$ (e.g., electrostimulation at $SP_1$).

At 460, a multi-site electrostimulation can be delivered to the selected sites, such as including $SP_1$ and $SP_2$. The electrostimulation can be delivered to the selected sites during the same cardiac cycle, simultaneously or separated by a specified temporal offset less than a sensed or paced interval value of a cardiac cycle. In an example, the information of the selected stimulation sites, along with other device information, can be displayed or otherwise presented in a human-perceptible medium format to a system user.

In an example, the method 400 can additionally include selecting one or more stimulation vectors from a plurality of candidate stimulation vectors. Each stimulation vector can include an anode and a cathode electrode. In an example, the cathode or the anode can include an electrode positioned at a selected site at a heart chamber (such as the LV). The one or more selected stimulation vectors can respectively include a cathode or an anode positioned at the selected stimulation sites $SP_x$. In an example, the one or more stimulation vectors can be selected using additional parameters including, for example, lead impedance as sensed between the stimulation electrodes, pacing threshold indicative of minimal energy required to capture the cardiac tissue, absence of or significance of phrenic nerve stimulation during stimulation, power consumption by stimulation and impact on longevity of the pulse generator, among others. Multi-site electrostimulation can then be delivered according to the selected one or more stimulation vectors.

Figure 5:
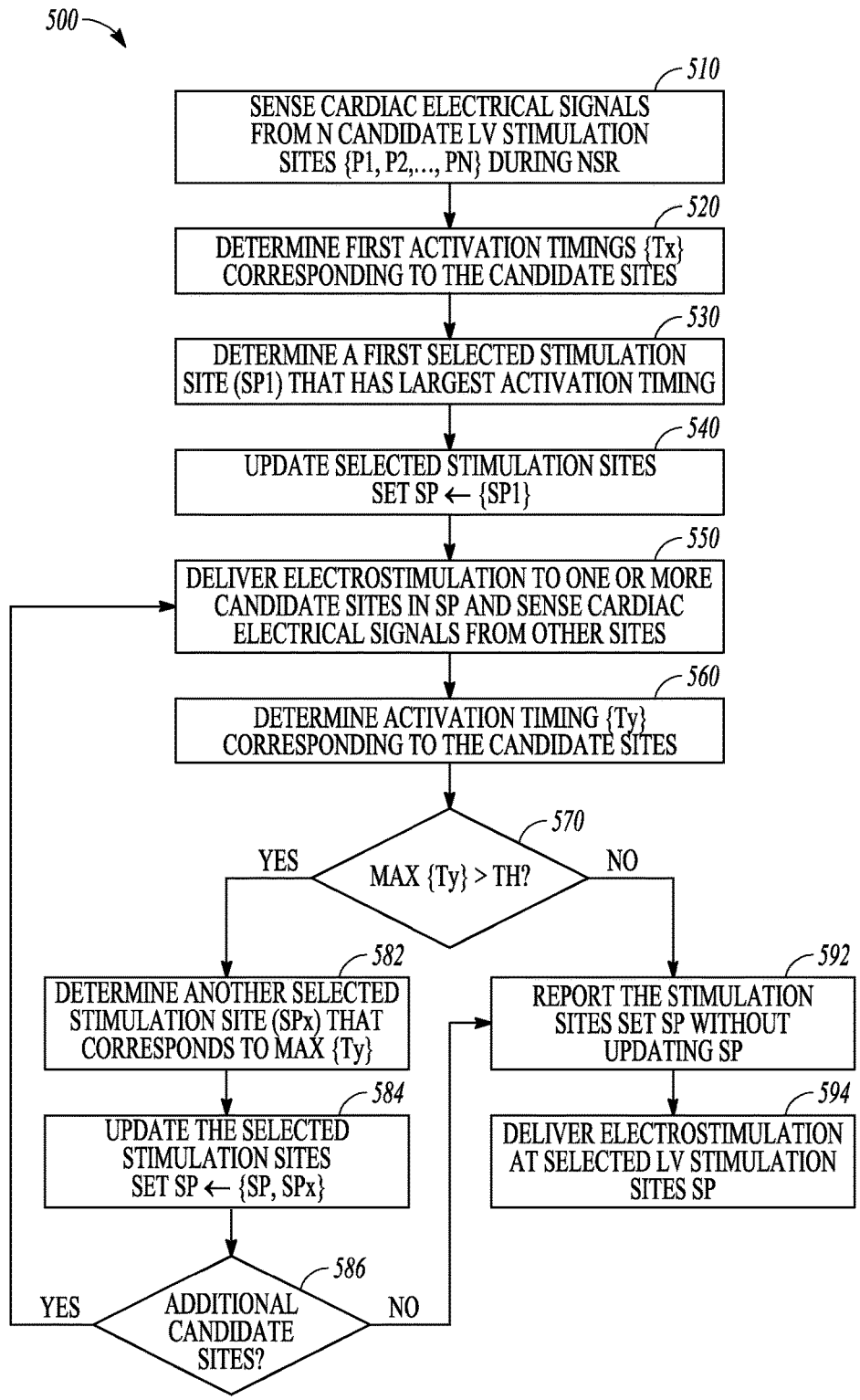
FIG. 5 illustrates an example of a method for multi-site LV pacing.

FIG. 5 illustrates an example of a method 500 for multi-site left ventricle (LV) stimulation. The method 500 begins at step 510, where a first set of N cardiac electrical signals can be sensed. The N cardiac electrical signals $X=\{X_1(t), X_2(t), \ldots, X_N(t)\}$, such as a surface ECG, a subcutaneous ECG, or an intracardiac EGM, can be sensed using a respective sensing vector comprising at least one LV sensing electrode placed at one of the N candidate LV stimulation sites $\{P_1, P_2, \ldots, P_N\}$ on a surface or within the chamber of the LV. The N cardiac electrical signals can be sensed when the heart undergoes an intrinsic rhythm such as a sinus rhythm. From each physiologic signal $X_i(t)$, a depolarization at the respective LV site $P_i$ can be detected, such as in response to an amplitude of the depolarization exceeding a specified intrinsic response threshold value.

At 520, first activation timings $\{Tx_1, Tx_2, Tx_N\}$, corresponding to the N candidate LV stimulation sites $\{P_1, P_2, \ldots, P_N\}$, can be computed using the detected depolarization. In an example, the activation timing $Tx_i$ can include a time interval between the detected depolarization at the LV site $P_i$ and a reference time. The reference time can include timing of a Q wave or timing of a sensed or paced activation at a site in the RV, so that the activation timing $T_i$ can indicate time delay from the Q wave or the RV activation to the sensed depolarization at the LV site $P_i$.

At 530, a first selected LV site ($SP_1$) can be determined as one of the N sites $\{P_1, P_2, \ldots, P_N\}$ that corresponds to the latest activation timing, such as the longest time delay from the Q wave or the RV activation to the detected depolarization at the LV sites $\{P_1, P_2, \ldots, P_N\}$. In an example, the first selected LV site ($SP_1$) is selected further in response to the latest activation timing exceeding a specified threshold. At 540, a selected stimulation sites set, SP, can be updated by including $SP_1$ into the set SP.

At 550, electrostimulation can be delivered to one or more candidate sites in the existing selected sites in SP. When SP contains only $SP_1$, electrostimulation can be delivered at $SP_1$, such as a unipolar of bipolar stimulation via a pacing vector comprising a stimulation electrode positioned at $SP_1$. A second set of cardiac electrical signals at the N candidate LV stimulation sites except $SP_1$. For example, if $SP_1$ is determined to be $P_k$, then N−1 cardiac electrical signals can be sensed at 550, $\{Y\}=\{Y_1(t), Y_2(t), \ldots, Y_{k-1}(t), Y_{k+1}(t), \ldots, Y_N(t)\}$, where $Y_i(t)$ denotes the signal sensed at the site $P_i$ during the electrostimulation at $SP_1$. From each of the physiologic signals $\{Y\}$ a respective repolarization at the respective LV site can be detected. At 560, second activation timings $\{Ty\}=\{Ty_1, Ty_2, \ldots, Ty_{k-1}, Ty_{k+1}, \ldots, Ty_N\}$, corresponding to the N−1 candidate LV stimulation sites $\{P_1, P_2, \ldots, P_{k-1}, P_{k+1}, \ldots, P_N\}$, can be computed using the detected depolarization. In an example, the activation timing $Ty_i$ can include a time interval between a detected depolarization at the respective LV site and the electrostimulation at $SP_1$.

At 570, the latest activation timing, such as the longest time delay from the electrostimulation at $SP_1$ to the detected depolarization at the LV sites, denoted by max{Ty}, can be identified. If max{Ty} does not exceed the specified threshold TH, then at 592 the SP is not updated, and the existing SP can be reported to the system user. However, if max{Ty} exceeds the specified threshold TH at 570, then at 582 the stimulation site $SP_x$ that corresponds to max{Ty} can be identified. At 584, the selected stimulation sites set SP can be updated by including $SP_x$. At 586, a check of the unselected candidate LV stimulations sites can be made. If there remains at least one candidate site, the stimulation site selection can be repeated at 550 to deliver electrostimulation to one or more selected sites in SP, and attempt to determine additional selected sites based on the evoked cardiac electrical signals from the unselected LV sites. When two or more selected sites are chosen to be stimulated (e.g., $SP_1$ and $SP_2$), the stimulation at 550 can be performed at the two or more selected sites simultaneously or asynchrony with a specified temporal offset less than a sensed or paced interval value of a cardiac cycle. However, if at 586, no additional candidate LV sites are available, the process continues at 592 by reporting the existing SP to the system user. At 594, multi-site LV electrostimulation can be delivered to selected sites in SP during a same cardiac cycle, either simultaneously or separated by a specified temporal offset less than a sensed or paced interval value of a cardiac cycle.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A cardiac electrostimulation system, comprising:
   an electrostimulation circuit, configured to deliver electrostimulation to two or more candidate sites in a left ventricle of a heart within a cardiac cycle; and
   a stimulation site selector circuit, in communication with the physiologic sensor circuit, configured to:
      sense intrinsic conduction at the two or more candidate sites;
      select a first site as a latest intrinsic activation among the two or more candidate sites;
      deliver electrostimulation at the first selected site; and
      select a second site as a latest activation among the two or more candidate sites in response to the delivered electrostimulation at the first selected site;
      wherein the electrostimulation circuit is configured to deliver electrostimulation to the first and second selected sites within a single cardiac cycle.

2. The system of claim 1, comprising a physiologic sensor circuit and two or more electrodes electrically coupled to the electrostimulation circuit, the two or more electrodes are removably and respectively positioned at two or more left ventricular (LV) sites, wherein:

the electrostimulation circuit is configured to deliver electrostimulation to the two or more LV sites using the respective two or more electrodes; and the physiologic sensor circuit is configured to sense respective physiologic signal from the two or more LV sites using the respective two or more electrodes.

3. The system of claim 2, wherein the two or more electrodes in LV are distributed on at least one lead configured to be placed in the LV and electrically coupled to the electrostimulation circuit.

4. The system of claim 2, wherein:

the physiologic sensor circuit is configured to sense respective cardiac electrical signals at the two or more LV sites during an intrinsic heart rhythm, and to detect respective depolarization at the two or more LV sites using the sensed cardiac electrical signals; and the stimulation site selector circuit is configured to:

determine first respective activation timings, for the two or more LV sites, using the detect respective depolarization at the two or more LV sites; and determine the first selected LV site that corresponds to a latest activation timing among the two or more LV sites.

5. The system of claim 4, wherein the stimulation site selector circuit is configured to determine the first respective activation timings including time intervals between a reference time and the detected depolarization at the two or more LV sites, the reference time including timing of a Q wave or timing of a sensed or paced activation at a right ventricle (RV).

6. The system of claim 2, wherein:

the physiologic sensor circuit is configured to sense respective cardiac electrical signals at the two or more LV sites during an electrostimulation of a site in a right atrium (RA), and to detect respective depolarization at the two or more LV sites using the sensed cardiac electrical signals;

the stimulation site selector circuit is configured to:

determine first respective activation timings including time intervals between the electrostimulation of the RA and the detected depolarization at the two or more LV sites; and determine the first selected LV site that corresponds to latest activation timing among the two or more LV sites.

7. The system of claim 2, wherein:

the physiologic sensor circuit is further configured to sense respective cardiac electrical signals at the two or more LV sites, other than the first selected LV site, during the electrostimulation of the first selected LV site, and to detect respective depolarization at the two or more LV sites using the sensed cardiac electrical signals; and the stimulation site selector circuit is further configured to:

determine second respective activation timings including time intervals between the electrostimulation at the first selected LV site and the detected depolarization at the two or more LV sites; and determine a second selected LV site that corresponds to latest activation timing among the two or more LV sites other than the first selected LV site, when the latest activation timing exceeds a specified threshold.

8. The system of claim 2, wherein:

the physiologic sensor circuit is further configured to sense respective cardiac electrical signals at the two or more LV sites, other than the first and second selected LV sites, during the electrostimulation of one or both of the first and second selected LV sites, and to detect respective depolarization at the two or more LV sites using the sensed cardiac electrical signals;

the stimulation site selector circuit is further configured to:

determine third respective activation timings including time intervals between the electrostimulation at one or both of the first and second selected LV sites and the detected depolarization at the two or more LV sites; and determine a third selected LV site that corresponds to the latest activation timing among the two or more LV sites other than the first and second selected LV sites, when the latest activation timing exceeds a specified threshold.

9. The system of claim 8, wherein the stimulation site selector circuit is configured to determine the third respective activation timings during one of simultaneous electrostimulation of both the first and second selected LV sites, or asynchronous electrostimulation of the first and second selected LV sites separated by a specified latency.

10. The system of claim 2, wherein:

the physiologic sensor circuit is further configured detect a first hemodynamic response to an electrostimulation of the first selected site, or a second hemodynamic response to an electrostimulation of the second selected site; and the stimulation site selector circuit is further configured to reconfirm the first selected site in response to the first hemodynamic response meeting a first specified criterion, or to reconfirm the second selected site in response to the second hemodynamic response meeting a second specified criterion.

11. The system of claim 1, further comprising a therapy controller circuit coupled to the electrostimulation circuit and the stimulation site selector circuit, the therapy controller circuit configured to program the electrostimulation circuit to deliver electrostimulation to the first and the second selected sites during a same cardiac cycle, simultaneously or separated by a specified temporal offset less than a sensed or paced interval value of a cardiac cycle.

12. The system of claim 1, further comprising a stimulation vector selector circuit configured to select two or more stimulation vectors from a plurality of candidate stimulation vectors, the selected two or more stimulation vectors respectively including an electrode positioned at the first selected site or the second selected site, and where electrostimulation circuit is configured to deliver electrostimulation according to the select two or more stimulation vectors.

13. A method for stimulating a heart using a cardiac electrostimulation system, the method comprising:

sensing intrinsic conduction at the two or more candidate sites in a left ventricle of a heart;

selecting, via the stimulation site selector circuit, a first site as a latest intrinsic activation among the two or more candidate sites;

delivering electrostimulation at the first selected site;

selecting, via the stimulation site selector circuit, a second site as a latest activation among the two or more candidate sites in response to the delivered electrostimulation at the first selected site; and delivering electrostimulation to the first and the second selected sites within the same cardiac cycle via an electrostimulation circuit.

14. The method of claim 13, wherein delivering electrostimulation includes delivering electrostimulation to the first and the second selected sites in the LV during the same cardiac cycle, simultaneously or separated by a specified temporal offset less than a sensed or paced interval value of the third cardiac cycle.

15. The method of claim 13, further comprising detecting respective depolarization at the two or more candidate sites using physiologic signals obtained during an intrinsic heart rhythm, wherein selecting the first site is based on time intervals between a reference time and the detected depolarization at the two or more candidate sites, the reference time including timing of a Q wave or timing of a sensed or paced activation at a right ventricle (RV).

16. The method of claim 13, further comprising detecting respective depolarization at the two or more candidate sites using physiologic signals obtained during the electrostimulation of the first selected site, wherein selecting the second site is based on time intervals between the electrostimulation at the first selected site and the detected depolarization at the two or more candidate sites.

17. The method of claim 13, wherein determining the second selected site includes determining the second selected site that corresponds to latest activation timing among the two or more candidate sites, other than the first selected site, when the latest activation timing exceeds a specified threshold.

18. The method of claim 13, further comprising:
delivering electrostimulation at one or both of the first and second selected sites; and
selecting a third site as a latest activation among the two or more candidate sites other than the first and second selected sites in response to the delivered electrostimulation at one or both of the first and second selected sites.

19. The method of claim 13, further comprising:
detecting a first hemodynamic response to an electrostimulation of the first selected site, or a second hemodynamic response to an electrostimulation of the second selected site; and
reconfirming the first selected site in response to the first hemodynamic response meeting a first specified criterion, or reconfirming the second selected site in response to the second hemodynamic response meeting a second specified criterion.

* * * * *